March 30, 1976 A. GROB Plant Pat. 3,852
KALANCHOE PLANT
Filed Sept. 25, 1974
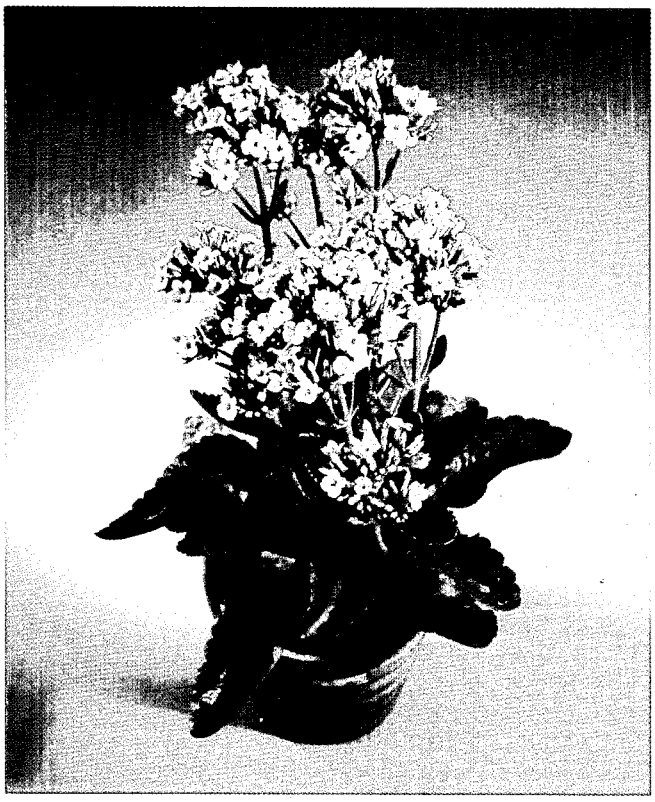

United States Patent

Plant Pat. 3,852
Patented Mar. 30, 1976

3,852
KALANCHOE PLANT

Adolf Grob, St. Gallen, Switzerland, assignor to Mikkelsens Inc., Ashtabula, Ohio Filed Sept. 25, 1974, Ser. No. 509,133
Int. Cl. A01h *5/00*
U.S. Cl. Plt.—68 1 Claim The present invention relates to a new and distinct variety of Kalanchoe plant known by the varietal name Saturn.

The new variety was discovered by me as a selected, cultivated seedling derived from Grobs Mars, the unpatented seed parent, and Kortesii, the unpatented pollen parent. The new cultivar was first asexually reproduced by vegetative cuttings at St. Gallen, Switzerland, and the unique characteristics of the new cultivar are transmitted through successive propagations.

The new cultivar is particularly characterized by its very intense orange colored flowers and its abundant flowering with relatively short response time, 12 weeks in summer and 14 weeks in winter. By means of short day treatment in the greenhouse, the new cultivar can be brought to flowering during the whole year. With respect to the parent cultivar Grobs Mars, the new cultivar has a more compact growth habit with very short but strong stems and good branching structure. By contrast, Grobs Mars has a relatively tall and slim growth habit. Saturn is relatively slow growing, requiring 2–3 additional weeks of growth before removal of apical tip to induce branching. Flowering is in eight to nine weeks after flower induction. The rate of growth is comparable to Solferino-purpur, disclosed in my pending application Ser. No. 509,-131, filed Sept. 25, 1974.

The following description is based on plants of the new cultivar grown initially in St. Gallen, Switzerland and subsequently in Ashtabula, Ohio. Flower color and foliage values are taken from the RHS Colour Chart.

The accompanying color photographic drawing shows a typical blooming plant of the new cultivar, with the color being as true as possible with color illustrations of this type.

Parentage: The new cultivar is a seedling resulting from crossing the seed parent Grobs Mars, an unpatented cultivar, with the pollen parent Kortesii, also an unpatented Kalanchoe variety.

Propagation: By asexually propagating by cuttings, it has been successfully demonstrated that the new cultivar is stable and produces true to type.

Form: Bush form, numerous branches; upright and compact; very short but strong stems.

Growth habit: Medium vigor; upright and compact giving a semi-dwarf appearance.

Rooting: The roots of the new cultivar are medium strong.

Blooming habit: Early response, reacts well to short day treatment.

Blooming season: Natural blooming season is January–February, although by short day treatment, flowering of the cultivar is possible year around.

Foliage: Leaves are opposite, borne at slight angle above horizontal, close internodes, being somewhat distinct in forming corky tissue on upper and lower sides in environments having high relative humidity, similar to geraniums having problems with edema.

*Size.*—Would be considered small when compared to the cultivar Mace; base of leaf is obtuse, petiole 15 mm. long, leaf 4–5 cm. wide by 7–8 cm. long.

*Shape.*—Elliptical, center vein quite pronounced on underside.

*Texture.*—Slightly rough on top, not as fleshy as other Grob cultivars.

*Margin.*—Crenate.

*Color.*—Upperside, near yellow green 147A. Underside, near green 137A.

Disease resistance: When grown within a group of plants infected with powdery mildew, Saturn appears to be quite resistant. No other diseases noted.

Flowers:

*Borne.*—On compound terminal paniculate cymes; main flowering stems are short, 10 cm. to 12 cm. and rigid. Nearly all flowers within each cyme are in flower at one time. Each flower is distinctly displayed giving a very attractive appearance.

*Quantity.*—Average for Kalanchoe cultivars.

*Flower buds.*—Firm, well formed, 5 mm. long before petals emerge, four sepals.

*Petals.*—Four petals (occasionally five) with considerable overlapping; the petals reflex to give true trumpet effect, measuring 7–8 mm. wide by 7–8 mm. long giving total flower diameter of 14–15 mm. Color is near orange-red 32A, fading to 28B–C. Midrib is distinct and usually a shade darker in color.

Reproductive organs:

*Stamens.*—Eight in number, fiilaments light green, others light brown.

*Pollen.*—Light yellow.

*Styles/ovaries.*—Light green, stigmas trun crystalline white when receptive; for carpels. Good seed producer.

I claim:

1. A new and distinct cultivar of Kalanchoe characterized particularly by its intense orange colored flowers; abundant flowering with short response time, 12 weeks in summer and 14 weeks in winter; its compact growth habit with short but strong stems, and by its ability to flower year round when given short day treatment in the greenhouse.

No references cited.

ROBERT E. BAGWILL, Primary Examiner